United States Patent
Bremer et al.

(10) Patent No.: US 6,402,932 B1
(45) Date of Patent: Jun. 11, 2002

(54) MEDIATED ELECTROCHEMICAL OXIDATION OF BIOLOGICAL WASTE MATERIALS

(76) Inventors: Bruce W. Bremer, 18300 Feathertree Way, Montgomery Village, MD (US) 20886-6318; Roger W. Carson, 8225 Madrillon Estates Dr., Vienna, VA (US) 22182

( * ) Notice: Subject to any disclaimer, the term of this patent is extended or adjusted under 35 U.S.C. 154(b) by 0 days.

(21) Appl. No.: 09/628,720

(22) Filed: Jul. 28, 2000

Related U.S. Application Data

(60) Provisional application No. 60/145,972, filed on Jul. 29, 1999.

(51) Int. Cl.[7] .............................. C02F 1/461; A62D 3/00
(52) U.S. Cl. ...................... 205/701; 205/688; 205/703; 205/746; 205/749; 588/204; 204/252; 204/259; 204/262; 204/263; 204/266
(58) Field of Search ................................ 205/688, 701, 205/703, 746, 749; 588/204; 204/252, 259, 262, 263, 266

(56) References Cited

U.S. PATENT DOCUMENTS 5,911,868 A * 6/1999 Balazs et al. ............... 205/703
5,919,350 A * 7/1999 Balazs et al. ............... 205/703
5,952,542 A * 9/1999 Steele ......................... 205/703

OTHER PUBLICATIONS

US4749519 (Patent Abstract) Jun. 7, 1988 Koehly et al.
US5516972 (Patent Abstract) May 14, 1996 Farmer et al.
US4810995 (Patent Abstract) Sep. 22, 1998 Soilleux et al.

* cited by examiner

Primary Examiner—Arun S. Phasge
(74) Attorney, Agent, or Firm—James Creighton Wray; Meera P. Narasimhan

(57) ABSTRACT

A mediated electrochemical oxidation process is used to treat, oxidize and dispose of biological waste materials. Waste materials are introduced into an apparatus for contacting the waste with an electrolyte, which comprises one or more oxidizing species in their higher valence states in aqueous solution. The electrolyte, which can be regenerated, is used to oxidize specific molecules of the waste materials, breaking them down and preventing the formation of dioxins. The waste treatment process takes place at a temperature range from room temperature up to a temperature slightly below the boiling point of the electrolyte solution (usually the temperature will be below 100° C.), and can be altered by adding ultraviolet radiation.

70 Claims, 2 Drawing Sheets

MEDIATED ELECTROCHEMICAL OXIDATION OF BIOLOGICAL WASTE MATERIALS

This application claims the benefit of Ser. No. 60/145,972, filed Jul. 29, 1999.

FIELD OF THE INVENTION

This invention relates generally to a process and apparatus for the disposal of biological waste which includes, but is not limited to, medical waste, infectious waste, pathological waste, animal waste, and sanitary waste and henceforth referred to as biological waste.

BACKGROUND OF THE INVENTION

The cost of disposing of biological waste in the U.S. is more than $5 billion per year. The capital cost of the equipment required is in the hundreds of millions of dollars. All institutions and businesses that generate and handle this category of waste have needs to provide safe effective and inexpensive disposal of the waste. In recent years there has been increasing concern over the disposal of biological waste. The two principal methodologies for the disposal of this waste are incineration and dumping in landfills.

The Environmental Protection Agency (EPA) has issued new regulations that require incinerators to reduce their emissions to very stringent levels for products that are exhausted from biological waste incinerators. The new regulations will, for practical purposes, close down or require major modifications to almost all such incinerators by the year 2001. Municipal landfills have already begun to refuse to accept biological waste especially if it is identifiable as medical waste. Most alternatives to these two methods involve thermal methods that emit products into the atmosphere that are not acceptable.

Biological waste is defined as any waste that is considered by any of, but not limited to, the following statutes and regulations:

New Jersey State Statute, "Comprehensive Regulatory Medical Waste Management Act", P.L. 1989, c. 34 (C.13.1E-48.13).

New York State Environmental Conservation Law, TITLE 15, "STORAGE, TREATMENT, DISPOSAL AND TRANSPORTATION OF REGULATED MEDICAL WASTE", Section 27-1501. Definitions.

New York State Public Health Law, TITLE XIII, "STORAGE, TREATMENT AND DISPOSAL OF REGULATED MEDICAL WASTE", Section 1389-aa. Definitions.

CALIFORNIA HEALTH AND SAFETY CODE, SECTION 117635. "Biohazardous Waste " Title 25 Health Services, Part I.

Texas Department of Health, Chapter 1 Texas Board of Health, "Definition, Treatment, and Disposition of Special Waste from Health Care-Related Facilities, Section 1.132 Definitions.

40 C.F.R. 60.51(c) PROTECTION OF ENVIRONMENT; Standards of performance for new stationary sources.

40 C.F.R. 240.101 PROTECTION OF ENVIRONMENT; Guidelines for the thermal processing of solid wastes (Section P only).

49 C.F.R. 173.134 TRANSPORTATION; Class 6, Division 6.2-Definitions, exceptions and packing group assignments.

33 C.F.R. 151.05 TITLE 33-"NAVIGATION AND NAVIGABLE WATERS; VESSELS CARRYING OIL, NOXIOUS LIQUID SUBSTANCES, GARBAGE, MUNICIPAL OR COMMERCIAL WASTE, AND BALLAST WATER";

Definitions (medical waste only).

Biological waste is a relatively new problem for today's technological society. The definition of this waste has been expanding in its coverage of materials that must be handled in a controlled manner. The foregoing list of state statutes and United States federal regulations are overlapping but necessary to accurately define the materials because no single statute or regulation covers all the materials to which this invention applies.

Mediated Electrochemical Oxidation (MEO) processes represent a mature science in the industrial complex over the past two decades. The orientation to date has been focused on the dissolution of transuranic metals and destruction of organics in mixed waste from the chemical reprocessing of irradiated nuclear reactor fuel, and controlled oxidation and destruction of organic-based military munitions and organophosphorus chemical weapon nerve agents, as is represented by patents dating back into the mid-eighties.

Research into the application of the MEO process to date has involved the use of the process to dispose of materials in these areas. In the first area, the MEO uses an electrochemical cell in which the electrolyte is generally restricted to a composition of nitric acid and silver ions. The silver ion serves as the regenerable mediating oxidizing species which is used in a oxidative dissolution of plutonium dioxide to recover plutonium contained in solid waste from processes, technological and laboratory waste (U.S. Pat. No. 4,749, 519), and subsequently extended to the dissolution of the plutonium dioxide component of mixed oxide fuel (coprecipitated uranium and plutonium oxide) (U.S. Pat. No. 5,745,835).

In the second area, the MEO process was used: (a) for the decomposition (i.e. oxidation) of organic matter contained in the mixed solid waste generated in extracting plutonium from irradiated nuclear reactor fuel (U.S. Pat. Nos. 4,874, 485; 4,925,643); (b) controlled oxidation of organic military munitions (U.S. Pat. No. 5,810,995); and (c) destruction of organophosphorus nerve agents (U.S. Pat. No. 5,855,763).

Both of the two areas discussed have involved similar use of the MEO process using nitric acid and silver ions being generated by an electrochemical cell with the anode and cathode being separated by a membrane. The two uses have differed in the temperature range used in each of the applications. The second use is operated between 50° C. and slightly below 100° C. to take advantage of the generation of the secondary oxidation species to assist in oxidizing organic materials. The first use is operated below 50° C. (generally around 25° C. or room temperature) to minimize Ag(II)—water reactions because unlike the Ag(II) ion, not all of the secondary oxidizing species have an oxidation potential sufficient to oxidize plutonium dioxide to a soluble species.

Others have substituted cerium and nitric acid, cobalt and nitric acid, and cobalt and sulfuric acid for the silver and nitric acid as the electrolyte (U.S. Pat. Nos. 5,516,972; 5,756,874). The temperatures vary among the three electrolytes being substituted for the silver and nitric acid combination. Most recently, ruthenium in a nearly neutral solution has been proposed as the electrolyte in a MEO process to decompose organic materials, which would operate between 50° C. and 90° C. (Platinum Review, Jul. 1998). All of the descriptions reviewed are similar in their application to the decomposition of organic materials and differ in their choice of electrolyte(s), pH, concentrations, and the operating temperature range over which they are applied.

These and other objects and features of the invention are apparent in the disclosure, which includes the above and ongoing written specification, with the drawings.

SUMMARY OF THE INVENTION

The invention relates to a method and apparatus for the mediated electrochemical oxidation (MEO) of wastes, such as biological materials and has particular application to, but is not limited to, biological waste, medical waste, infectious waste, pathological waste, animal waste, and sanitary waste (henceforth collectively referred to as biological waste).

A mediated electrochemical oxidation process involves an oxidizing electrolyte, wherein at least one oxidizing species is electrochemically generated in an electrochemical cell. A membrane in th e electrochemical cell separates the anolyte and catholyte. The preferred MEO process uses as mediator ions, for example, the following metals: Ag, Ce, Co, Fe, Mn or Ru in nitric acid, sulfuric acid or phosphoric acid as the anolyte. A cost reduction can be achieved in the a basic MEO process by using anions that are useable in alkaline solutions such as NaOH and KOH, since the oxidation potentials usually decrease with increasing pH. The catholyte may contain the same acid as the anolyte, but not necessarily in the same concentration. The process operates over the temperature range from room temperature up to a temperature slightly below the boiling point of the electrolyte solution (usually the temperature will be below 100° C.) during the destruction of the biological waste.

The MEO process begins with the electrochemical oxidation of the dissolved mediator ions to one of their higher valence states, after which these ions oxidize the biological waste and are themselves reduced down to their initial lower valence state, whereupon they are again electrochemically oxidized back up to their higher valence state. In the case of some higher valence oxidized species, a second oxidation process is possible.

At higher temperatures (i.e., above about 50° C.) these higher valence oxidizer species react with the aqueous solution to produce a variety of powerful oxidizing free radicals (e.g., .OH, etc.) and hydrogen peroxide, etc. Decomposition of the hydrogen peroxide into free hydroxyl radicals is well known to be promoted by ultraviolet irradiation. The MEO process biological waste destruction rate using these species, therefore, will be increased by ultraviolet irradiation of the reaction chamber anolyte.

The principals of the oxidation process in which the hydroxyl free radical cleaves chemical bonds and oxidizes organic compounds have been widely documented, resulting in the formation of successively smaller chained hydrocarbon compounds. The intermediate compounds formed are easily oxidized to carbon dioxide and water during sequential reactions.

One distinction between the prior art and this invention is in the application to biological waste, which distinctly differs from all prior applications. The prior art processes and their supporting patents may focus on organic materials, but they clearly distinguish from biological waste both in describing their processes and specifically in the examples of materials being treated by their processes. The materials are generally characterized as complex organic molecules associated with industrial processes. The prior art does not describe or refer to a single process that is biological in nature. Prior art processes that specifically deal with biological waste do not use the MEO process to dispose of those categories of waste.

DETAILED DESCRIPTION OF PREFERRED EMBODIMENTS

MEO Chemistry

Mediated Electrochemical Oxidation (MEO) process chemistry described in this patent uses one or more of the following metallic ions: silver, cerium, cobalt, iron, manganese and ruthenium in the anolyte as the mediator. The catholyte is composed of one of the following acids; nitric, sulfuric, or phosphoric.

The MEO Apparatus is unique in that it accommodates the numerous choices of mediator metallic ions and acids by draining, flushing, and refilling the system with the electrolyte of choice.

Because of redundancy and similarity in the description of the various metallic ions, only the iron and nitric acid combination is discussed in detail. The Fe (VI) ion (i.e. $FeO_4^{-2}$ species) has an oxidation potential sufficient to react with water to produce secondary oxidation species (e.g., hydroxyl free radicals, etc.). The remainder of this discussion addresses the more complex Fe (VI) process as it not only addresses the oxidation due to the metal ions but also the secondary oxidation species.

Figure 1:
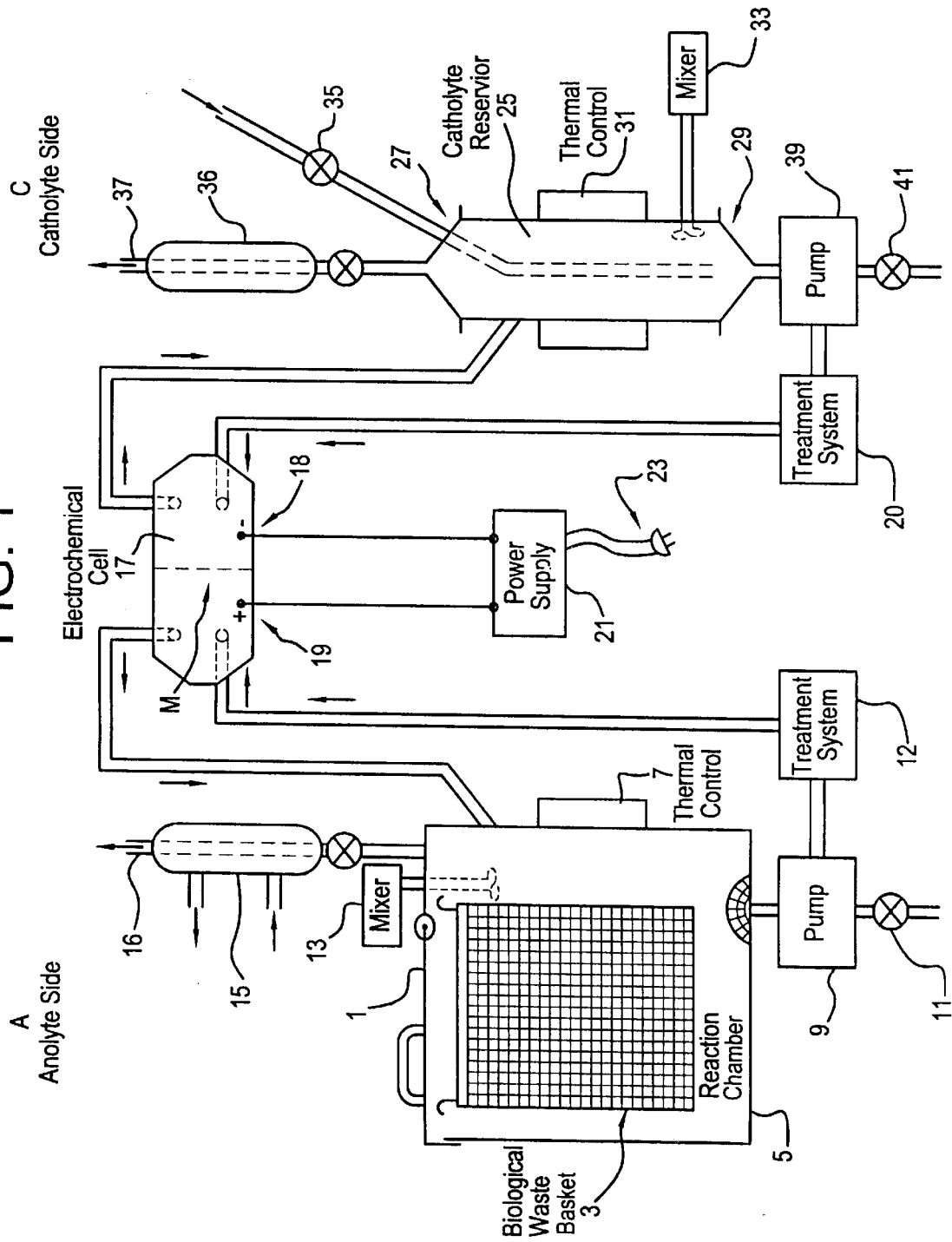
FIG. 1 is a schematic representation of a system for destroying biological waste materials.

FIG. 1 shows an MEO Apparatus in a schematic representation of the system for destroying biological waste. At the anode of the electrochemical cell 17 Fe (III) ions ($Fe^{30}_3$, ferric) are oxidized to Ag Fe (VI) ions ($FeO_4^{-2}$, ferrate),

$$Fe^{-3} + 4H_2O \rightarrow FeO_4^{-2} - 8H^- + 3e^-$$

the anolyte temperate is sufficiently high, typically above 50° C., the Fe (VI) species may undergo a redox reaction with the water in the aqueous anolyte. The oxidation of water proceeds by a sequence of reactions producing a variety of intermediate reaction products, some of which react with each other. A few of these intermediate reaction products are highly reactive free radicals including, but not limited to the hydroxyl (.OH) and hydrogen peroxy (.$HO_2$) radicals. Additionally, the mediated oxidizer species ions may interact with the stated acid in the anolyte ($HNO_3$, $H_2SO_4$, or $H_3PO_4$) to produce free radicals typified by, but not limited to .$NO_3$. Another possible source of free radicals from the electrolyte acids is the direct oxidation of the $NO_3^-$, $SO_4^{-2}$, or $PO_4^{-3}$ ions at the anode of the cell. The population of hydroxyl free radicals may be increased by ultraviolet irradiation of the anolyte in the reaction chamber to cleave the hydrogen peroxide molecules, intermediate reaction products, into two such radicals.

These secondary oxidation species in conjunction with Fe (VI) ions oxidize the biological materials.

The oxidizers react with the biological waste to produce $CO_2$ and water. These processes occur in the anolyte on the anode side of the system in the reaction chamber 5. Addition of iron ions to non-iron-based MEO systems are also proposed as this has the potential for increasing the overall rate of medical waste oxidation compared to the non-iron MEO system alone. The electrochemical oxidation proceeds much faster for iron ions than for most other mediator ions. Therefore, if the two step process of electrochemically forming an $FeO_4^{-2}$ ion and the $FeO_4^{-2}$ ion oxidizing the mediator ion to its higher valence occurs faster than the direct electrochemical oxidation of the mediator ion, then there is an overall increase in the rate of biological waste destruction.

Membrane M separates the anode and the cathode chambers in the electrochemical cell. Hydrogen ions ($H^+$)travel through the membrane M due to the electrical potential from the power supply 21 applied between the electrodes 18 and 19. In the catholyte the nitric acid is reduced to nitrous acid

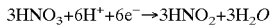
$$3HNO_3+6H^++6e^-\rightarrow 3HNO_2+3H_2O$$

by the reaction between the $H^+$ ions and the nitric acid. Oxygen is introduced into the catholyte through the air sparge 35, and the nitric acid is regenerated,

$$3HNO_2+3/2O_2\rightarrow 3HNO_3$$

The overall process results in the biological waste being converted to carbon dioxide, water, and a small amount of inorganic compounds in solution or as a precipitate.

The biological waste may be a liquid, solid, or a mixture of solids and liquids. The biological waste is introduced into the top of biological waste basket 3 in the reaction chamber 7. The apparatus continuously circulates the anolyte portion of the electrolyte through the reaction chamber to promote maximum contact area between the waste and the oxidizing species. Contact of the oxidizing species with incomplete oxidation products that are gaseous at the conditions within the reaction chamber 5 may be enhanced by using conventional techniques for promoting gas/liquid contact 7 (e.g., ultrasonic vibration, mechanical mixing). All surfaces of the apparatus in contact with the anolyte or catholyte are composed of stainless steel or nonreactive polymers such as PTFE (Teflon™).

The anolyte circulation system contains a pump 9 and a removal and treatment system 12 (e.g., filter, centrifuge, hydrocyclone, settling tank, etc.) to remove any precipitate or other insoluble inorganic compounds that form as a result of mediator ions (e.g., Ag, Ce, Co, Fe, Mn, Ru) reacting with the small amount of chlorine (or other anions) that may be present in the waste stream. The anolyte is returned to the electrochemical cell 17, which completes the circulation in the anode side (A).

Waste may be added to the basket 3 in the reaction chamber either continuously or in the batch mode. The anolyte starts either at the operating temperature or at a lower temperature, which subsequently is increased by the thermal control 7 to the desired operating temperature for the specific waste stream. Waste may also be introduced into the apparatus, with the concentration of electrochemically generated oxidizing species in the anolyte being limited to some predetermined value between zero and the maximum desired operating concentration for the waste stream by control of the electric current by the system power supply 23 supplied to the electrochemical cell 17. The electrolyte is composed of an aqueous solution of mediator ions and acid (nitric, phosphoric, or sulfuric acid) and is operated over the temperature range from room temperature to slightly below the boiling point of the electrolytic solution (usually less than 100° C.).

Considerable attention has been paid to halogens and their interactions with silver ions, which are of much less importance to this invention. The biological waste contains relatively small amounts of these halogen elements compared to the halogenated solvents and nerve agents addressed in the cited patents. Silver ions are required to oxidize those organic compounds in the cited patents while in this patent there is a choice of mediator ions. The choice of mediator ions effects the cost of the electrolyte and may be used to avoid formation of insoluble inorganic compounds thereby preventing removal of the mediator.

The residue of the inorganic compounds is flushed out of the treatment system 12 during periodic maintenance if necessary. If desired inorganic compounds may be recovered from the process stream using any one of several chemical or electrochemical processes. The apparatus operates across the temperature range from room temperature to slightly below the boiling point of the electrolyte (generally below 100° C.) adjusted to the composition of the materials introduced in to the reaction chamber. The system is monitored for the production of $CO_2$ as a means of determining when the decomposition process is complete.

The entireties of U.S. Pat. Nos. 4,749,519; 4,874,485; 4,925,643; 5,745,935; 5,810,995; and 5,855,763 are included herein by reference for their relevant teachings.

MEO Apparatus

A schematic drawing of the MEO apparatus shown in FIG. 1 illustrates the application of the MEO process to the destruction of biological waste. The lid 1 is raised and the biological waste is placed or poured into the basket 3 in the reaction chamber 5 as liquid, solid, or a mixture of liquids and solids. A small thermal control unit is connected to the reaction chamber 5 to heat or cool the anolyte to the selected temperature range.

The anolyte portion of the electrolyte solution contains mediated oxidizer species and secondary oxidizing species. The anolyte is circulated into the reaction chamber from the electrochemical cell 17 by pump 9. The anolyte portion and catholy te portion of the electrolyte are separated by a membrane M in the electrochemical cell 17. The electrochemical cell 17 is powered by a DC power supply 21 typically delivering 2 to 6 volts. The DC power supply 21 operates off a typical 110 volt or 220 volt AC line.

The electrolyte containment boundary is composed of materials resistant to the oxidizing electrolyte (e.g., stainless steel, PTFE, PTFE lined stainless steel, etc.). Reaction products resulting from the oxidizing processes being conducted on the anolyte side (A) of the system that are gaseous at the anolyte operating temperature and pressure are discharged to the condenser 15. The more easily condensed products of incomplete oxidation are separated from the off gas stream 16 and are returned to the anolyte reaction chamber for further oxidation. The noncondensible incomplete oxidation products (e.g., low molecular weight organics, carbon monoxide, etc.) are reduced to acceptable levels for atmospheric release by a gas cleaning system 15.

Various scrubber/absorption columns are used or the gas mixture is recontacted with the anolyte to provide adequate reaction time and contact area to ensure the required degree of oxidation, if necessary. A major product of the oxidation process is $CO_2$, which is vented 16 out of the system. An optional inorganic compound removal and treatment systems 13 is used should there be more than trace amount of chlorine, or other precipitate forming anions present in the biological waste being processed.

A pump 39 circulates the catholyte portion of the electrolyte through the portion of the electrochemical cell 17 on the cathode side of the membrane. The catholyte portion of the electrolyte flows into a catholyte reservoir 25. A small thermal control unit 31 is connected to the catholyte reservoir 25 to heat or cool the catholyte to the selected temperature range. External air is introduced through an air sparge 35 into the catholyte reservoir 25. The oxygen contained in the air oxidizes nitric acid and the small amounts of nitrogen oxides produced by the cathode reactions to nitric acid and $NO_2$, respectively. Contact of the oxidizing gas with nitrous acid may be enhanced by using conventional techniques for promoting gas/liquid contact by a mixer 33 (e.g., ultrasonic vibration, mechanical mixing, etc.). Systems using non-nitric acid catholytes may also require air sparging to dilute and remove off gas such as hydrogen. An off gas cleaning system 36 is used to remove any unwanted gas products (e.g. $NO_2$, etc.). The cleaned gas stream, combined with the unreacted components of the air introduced into the system is discharged through the off gas vent 37. Optional mediated oxidizer species recovery (i.e. metallic ions) and treatment system 20 is positioned on the catholyte side. Some mediated oxidizer species may cross the membrane M in small amounts, and this option is available if it is necessary to recover the species (i.e. metallic ions).

Figure 2:
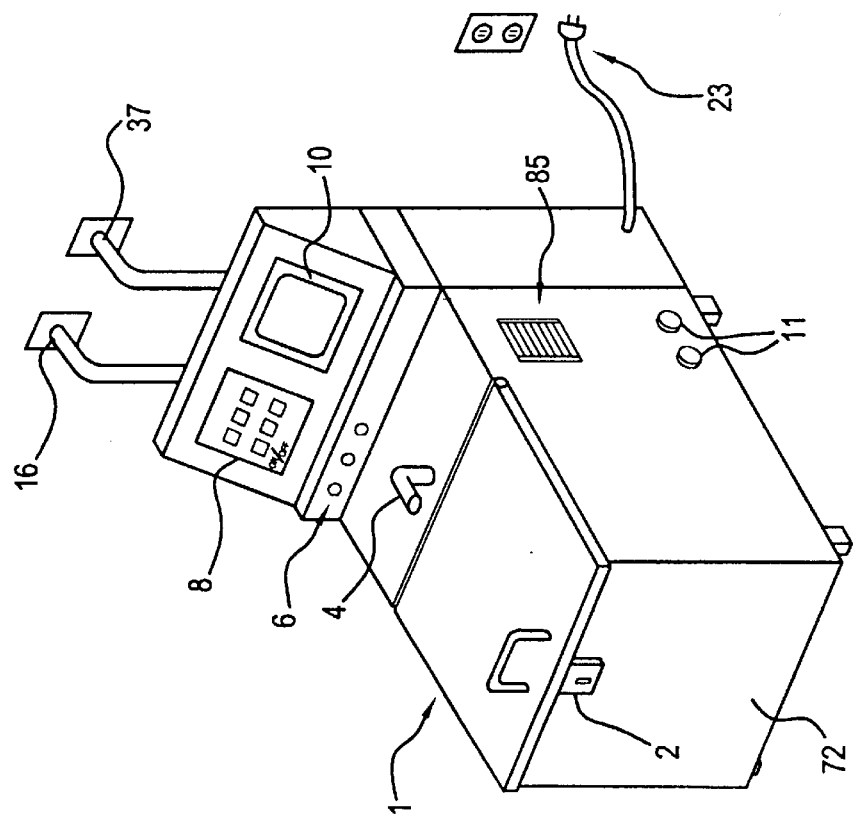
FIG. 2 is a schematic representation of the preferred embodiment.

In a preferred embodiment shown in FIG. 2, System Model 1.0 is sized for use in a medical office or laboratory. Other systems are similar in nature but are scaled up in size to handle a larger capacity of waste, such as patient's room, operating room, laboratories, etc.

The system has a control keyboard 8 for input of commands and data. There is a monitor screen to display the systems operation and functions. Below these controls are the status lights 6 for on, off, and standby. Hinged lid 1 is opened and the biological waste is deposited in the basket 3 in the chamber 7. A lid stop 2 keeps the lid opening controlled. In the chamber is the aqueous acid and mediated oxidizer species solution in which higher valence oxidizer species initially may be present or may be generated electrochemically after introduction of the waste and application of power 23 to the cell 17. Power supply 21 provides direct current to an electrochemical cell 17. Pump 9 circulates the anolyte portion of the electrolyte and the biological waste material is rapidly oxidized at room temperature and ambient pressure. The oxidation process will continue to break the materials down into less and less complex molecules until they reach $CO_2$, water, and some trace inorganic salts. Any residue is passified in the form of a salt and may be periodically removed through the flush and drain outlets 11. The electrolyte may be changed through this same plumbing. The catholyte reservoir has two flange joints 27 and 29, which allow access to the reservoir for cleaning.

Due to low power consumption and low consumption of mediated oxidizer species and electrolyte acid the device may remain activated throughout the day, and biological waste may be added as it is generated. The compactness of the device makes it ideal for offices and surgeries as well as suitable for use with high volume inputs of laboratories and hospitals. The process operates at low temperature and ambient atmospheric pressure and does not generate toxic compounds during the destruction of the biological waste, making the process indoor compatible. The system is scalable to a unit large enough to replace a hospital incinerator system. The $CO_2$ oxidation product is vented out the wall vent 16, and the atmospheric air vent 37 for the cathode side is shown.

Steps of the Operation of the MEO Process

Figure 3:
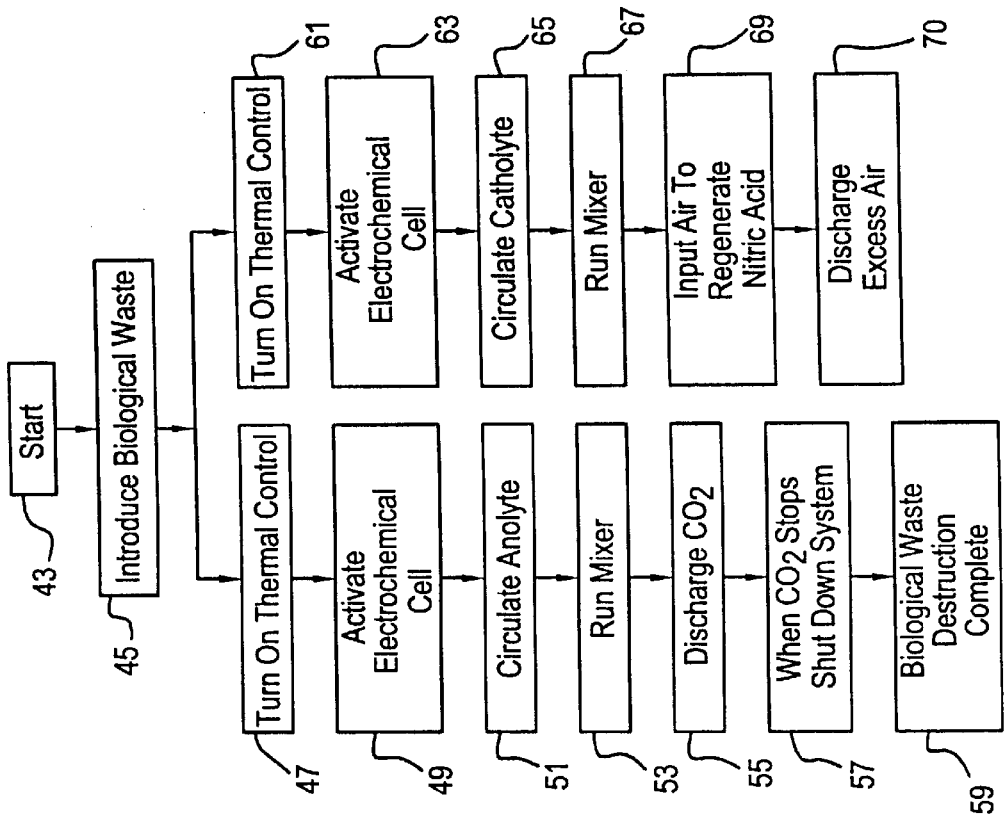
FIG. 3 is a schematic representation of the steps of the process used in the apparatus.

FIG. 3 is a schematic of the steps in the operation of process of destroying biological waste in the System Model 1.0. The system is started 43 by engaging the "On" button on the control keyboard 8. The monitor screen 10 displays the steps of the process in the proper sequence. The lid 1 is opened and the biological waste is placed 45 in the basket. The thermal controls 7 and 31 are turned on 47/61, which brings the electrolyte in to the temperature range for proper function. The electrochemical cell is energized 49,63. The pumps 9 and 39 begin to circulate 51,65 the anolyte and catholyte respectively.

As soon as the electrolyte circulation is flowing throughout the system, the mixers begin to operate 53 and 67. The biological waste is being decomposed into water and $CO_2$, which is discharged 55 out of the $CO_2$ vent 16. Air is drawn 69 into the catholyte reservoir 25, and excess air is discharged 70 out the atmospheric vent 37. When the $CO_2$ production ceases, the biological waste has been fully destroyed 57, and the system goes to standby 59.

EXAMPLE

Example (1)

The device performance parameters may be estimated for medical/pathological waste by analyzing the electrochemical oxidation of human protoplasm, stated in the literature to consist of 67 weight % water, 29 weight % organic solids and 4 weight % minerals. These organic solids are composed of proteins (15 weight %), lipids (13 weight %) and carbohydrates (1 weight %). For this analysis it is assumed the protein is collagen ($C_{102}H_{149}O_{38}N_{31}$), the lipids, or fats ($C_{57}H_{110}O_6$) and the carbohydrates are glucose units ($C_6H_{12}O_6$), and the oxidation products are $H_2O$, $CO_2$ and $NO_2$. Assuming a 3-volt cell potential and 100percent current efficiency, it requires 8.2 kWh to oxidize 1-kg human protoplasm. The time required may be determined by (1) the electrode surface area of the cell (i.e., 0.5 amp/cm$^2$ current density limit) and (2) the capacity of the power supply at 3 volts.

Anolyte is in the range of 1 to 22 M nitric acid, typically about 4 to 8M nitric acid, 0.01 to a saturated solution of a soluble iron (ferric) typically 0.5M soluble iron ferric salt (usually but not limited to ferric nitrate). If augmented by the addition of a soluble Ag, Ce, Co, Mn, or Ru salt in the range 0.1 to a saturated solution, the lower limit of the soluble iron salt concentration may be reduced to 0.001 M. Catholyte is in the range of 1 to 22 M nitric acid, typically about 4 to 8M nitric acid. The apparatus is operated between room temperature and slightly below the boiling point. In the alternative acids case the range of 1–19 M sulfuric and phosphoric acids for mediators soluble in them in the same concentration ranges for $Fe^{+3}$.

Example (2)

The MEO process produces $CO_2$, water, and trace inorganic salts, all of which are considered benign for introduction into the environment by regulatory agencies. The cost of using the MEO process in this invention is competitive with both the incineration and landfill methodologies. The MEO process is uniquely suited for destruction of biological waste because water, which constitutes a major portion of this waste (e.g., tissue, bodies fluids, etc.) is actually a source of secondary oxidizing species rather than parasitic reactions competing for the mediator oxidizer specie s. Furthermore, the energy that must be provided in the MEO process to heat the waste stream water component from ambient to the electrolyte operating temperature (i.e., 80° C. maximum temperature increase) is trivial compared to the water enthalpy increase required in autoclave or incineration based processes.

Example (3)

The system is unique relative to earlier art, since it is built to operate in a hospital room or laboratory where it must be compatible with people working in close proximity to the system as well as next to people being treated for medical conditions.

Example (4)

The system is built to require limited skill to operate it. The system needs to be accessed during it s operating cycle so that more biological waste may be added and needs to remain compatible with the room environment.

Example (5)

The system is built to operate with materials that are safe to handle in the environment in which it is to be used. The biological waste contains little or no substances that react with our choice of electrolytes to produce volatile compounds that would offer a problem in the room environment. The system may operate at temperatures less then 100° C. and at ambient atmospheric pressure, which adds to the indoor compatibility.

Example (6)

The simplicity of the new system built for use with biological waste produces a system less expensive to operate and cleaner to use than existing waste treatments. The system complexity is reduced by comparison to previous MEO system, since there is not a requirement to deal with quantities of halogens. The system is truly a green machine' in the sense of an environmentally benign system.

Example (7)

The system is built so that the composition of the electrolyte may be changed to adapt the system to a selected composition of the biological waste stream.

Example (8)

The system flexibility provides for the introduction of more then one metallic ion resulting in marked improvement in the efficiency of the electrolyte. Furthermore, it desensitizes the electrolyte to chlorine ions in solution.

While the invention has been described with reference to specific embodiments, modifications and variations of the invention may be constructed without departing from the scope of the invention.

We claim:

1. A process for treating and oxidizing biological waste materials comprising disposing an electrolyte in an electrochemical cell, separating the electrolyte into an anolyte portion and a catholyte portion with a hydrogen ion-permeable membrane or porous polymer, ceramic or glass membrane, applying a direct current voltage between the anolyte portion and the catholyte portion, disposing a foraminous basket in the anolyte, placing or pouring the biological waste materials in the basket within the anolyte portion, and oxidizing the biological waste materials in the anolyte portion with a mediated electrochemical oxidation (MEO) process, wherein the anolyte portion further comprises an oxidizing species in aqueous solution and the electrolyte is an acid or neutral aqueous solution.

2. The process of claim 1, wherein each of the oxidizing species has normal valence states and higher valence oxidizing states and further comprising creating the higher valence oxidizing states of the oxidizing species by stripping and reducing electrons off normal valence state species in the electrochemical cell.

3. The process of claim 1, further comprising introducing an ultrasonic energy into the anolyte portion rupturing cell membranes in the biological waste materials by raising local temperature of the cell membranes with the ultrasonic energy to above several thousand degrees and causing cell membrane failure.

4. The process of claim 1, further comprising introducing ultraviolet energy into the anolyte portion and decomposing hydrogen peroxide into free hydroxyl radicals therein and increasing efficiency of the MEO process by recovering energy through the oxidizing of the biological waste materials in the anolyte portion.

5. The process of claim 1, further comprising using oxidizing species found in situ in the process, by converting normal valence state species found in situ in solution into higher valence state species and destroying the biological waste materials with the higher valence state species.

6. The process of claim 1, further comprising using oxidizing species, and attacking specific organic molecules with the oxidizing species and preventing the formation of dioxins.

7. The process of claim 1, further comprising interchanging oxidizing species in a preferred embodiment without changing equipment.

8. The process of claim 1, further comprising breaking down biological waste materials into organic compounds and attacking the organic compounds using inorganic free radicals and generating organic free radicals.

9. The process of claim 1, further comprising energizing the electrochemical cell at a potential level approximately equal to ion valence potential or slightly higher.

10. The process of claim 1, further comprising raising normal valence state species to a higher valence state and stripping the normal valence state species of electrons in the electrochemical cell.

11. The process of claim 1, further comprising circulating anions through a converter.

12. The process of claim 1, further comprising contacting anions with biological waste materials in the anolyte portion.

13. The process of claim 1, further comprising introducing biological waste materials into the anolyte portion.

14. The process of claim 1, further comprising reducing higher valence state species to normal valence state species and decomposing molecules from oxidizer material.

15. The process of claim 1, further comprising circulating anions through the electrochemical cell.

16. The process of claim 1, further comprising involving increasing the anolyte temperature above 50° C. thereby initiating reactions between the mediator and water to form the free radical secondary oxidizing species and hydrogen peroxide.

17. The process of claim 1, further comprising adding an ultraviolet source to the anolyte portion and augmenting secondary oxidation processes, breaking down hydrogen peroxide into free hydroxyl radicals, and increasing oxidation processes.

18. The process of claim 1, characterized in that the process is performed at a temperature between room temperature and slightly below the boiling point of the electrolyte (generally below 100° C.).

19. The process of claim 1, wherein the temperature at which the process is performed is varied.

20. The process of claim 1, wherein the oxidizing species is chosen from the group consisting of silver, cerium, cobalt, iron, manganese, ruthenium, and combinations thereof.

21. The process of claim 1, wherein the aqueous solution is chosen from the group consisting of nitric acid, sulfuric acid, phosphoric acid.

22. The process of claim 1, further comprising removing and treating precipitate-forming anions from the biological waste.

23. The process of claim 1, further comprising introducing more than one mediated oxidizing ion into the anolyte portion.

24. The process of claim 1, further comprising regenerating the anolyte portion.

25. An apparatus for treating and oxidizing biological waste materials comprising an electrochemical cell, an electrolyte disposed in the electrochemical cell, a hydrogen ion-permeable membrane or porous polymers, ceramic, or a glass membrane disposed in the electrochemical cell for separating the cell into anolyte and catholyte chambers and separating the electrolyte into anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, a foraminous basket disposed in the anolyte chamber for receiving the biological waste materials, an oxygen source connected to the electrochemical cell for promoting the oxidizing of the biological waste materials in the anolyte portion with a mediated electrochemical oxidation (MEO) process wherein the anolyte portion includes an oxidizing species in aqueous solution and the electrolyte is an acid, alkaline or neutral aqueous solution.

26. The apparatus of claim 25, wherein each of the oxidizing species has normal valence states and higher valence oxidizing states and wherein the higher valence oxidizing states of the oxidizing species is created by stripping and reducing electrons off normal valence state species in the electrochemical cell.

27. The apparatus of claim 25, further comprising an ultraviolet source connected to the anolyte chamber and decomposing hydrogen peroxide into free hydroxyl radicals therein and increasing efficiency of the MEO process by recovering energy through the oxidizing of the biological waste materials in the anolyte chamber.

28. The apparatus of claim 25, further wherein the oxidizing species are higher valence state species found in situ for destroying the biological waste material.

29. The apparatus of claim 25, further comprising organic free radicals for aiding the MEO process and breaking down the biological waste materials into organic compounds.

30. The apparatus of claim 25, wherein the hydrogen ion-permeable membrane or porous polymers, ceramic, or glass membrane comprises a filter for separating the anolyte portion and the catholyte portion.

31. The apparatus of claim 25, wherein the electrochemical cell is energized at a potential level of at least ion valence potential.

32. The apparatus of claim 25, further comprising a converter connected to the anolyte chamber.

33. The apparatus of claim 25, further comprising involving anions with an oxidation potential sufficient to initiate secondary oxidation process as thereby producing additional oxidizers.

34. The apparatus of claim 25, further comprising an ultraviolet source connected to the anolyte for augmenting secondary oxidation processes by breaking down hydrogen peroxide into free hydroxyl radicals for increasing oxidation processes.

35. The apparatus of claim 25, wherein oxidation and reduction potentials of the oxidizing species are inversely related to pH.

36. The apparatus of claim 25, wherein the oxidizing specie is chosen from the group consisting of silver, cerium, cobalt, iron, manganese, ruthenium, and combinations thereof.

37. The apparatus of claim 25, wherein the aqueous solution is chosen from the group consisting of nitric acid, sulfuric acid, phosphoric acid, and combinations thereof.

38. The apparatus of claim 25, further comprising a $CO_2$ vent for releasing $CO_2$ atmospherically.

39. The apparatus of claim 25, further comprising a reaction chamber housing the anolyte portion and the foraminous basket.

40. The apparatus of claim 39, further comprising a thermal control connected to a reaction chamber for varying the temperature of the anolyte portion.

41. The apparatus of claim 39, further comprising a condenser connected to the reaction chamber.

42. The apparatus of claim 39, further comprising a lid attached to the reaction chamber allowing insertion of waste into the anolyte portion.

43. The apparatus of claim 42, further comprising a lid stop connected to the lid for controlling movement of the lid.

44. The apparatus of claim 39, further comprising a filter connected to the reaction chamber.

45. The apparatus of claim 39, further comprising an anolyte pump connected to the reaction chamber for circulating the anolyte portion back to the electrochemical cell.

46. The apparatus of claim 45, further comprising a drain connected to the anolyte pump.

47. The apparatus of claim 46, further comprising a drain valve connected to the drain.

48. The apparatus of claim 39, further comprising an inorganic compounds removal and treatment system connected to the anolyte pump.

49. The apparatus of claim 25, further comprising a catholyte reservoir connected to the cathode portion of the electrochemical cell.

50. The apparatus of claim 49, further comprising an air sparge connected to the catholyte reservoir for introducing air into the catholyte reservoir.

51. The apparatus of claim 49, further comprising an off gas cleaning system for cleaning gases before release into the atmosphere connected to the catholyte reservoir.

52. The apparatus of claim 51, wherein the off gas cleaning system comprises scrubber/absorption columns.

53. The apparatus of claim 51, further comprising an atmospheric vent for releasing gases into the atmosphere connected to the off gas cleaning system.

54. The apparatus of claim 51, further comprising a flange joint on the catholyte reservoir to facilitate flushing out the catholyte reservoir.

55. The apparatus of claim 51, further comprising a thermal control unit connected to the catholyte reservoir for varying the temperature of the catholyte portion.

56. The apparatus of claim 51, further comprising a mixer for stirring the catholyte connected to the catholyte reservoir.

57. The apparatus of claim 51, further comprising a catholyte pump for circulating catholyte back to the electrochemical cell connected to the catholyte reservoir.

58. The apparatus of claim 51, further comprising a drain for draining catholyte connected to the catholyte pump.

59. The apparatus of claim 51, further comprising a drain valve connected to the drain.

60. The apparatus of claim 51, further comprising a metal recovery and acid treatment system connected to the catholyte pump.

61. The apparatus of claim 25, further comprising a housing surrounding the electrochemical cell, the electrolyte, and the foraminous basket.

62. The apparatus of claim 61, further comprising a monitor screen connected to the housing for displaying information about treating the biological waste materials.

63. The apparatus of claim 61, further comprising a control keyboard connected to the housing for inputting data for treating the biological waste materials.

64. The apparatus of claim 61, further comprising status lights connected to the housing for displaying information about treating the biological waste materials.

65. The apparatus of claim 61, further comprising an air intake vent connected to the housing for introducing air to an air sparge.

66. The apparatus of claim 61, further comprising an external $CO_2$ vent connected to the housing for releasing $CO_2$ into the atmosphere.

67. The apparatus of claim 61, further comprising an external atmospheric vent connected to the housing for releasing gases into the atmosphere.

68. The apparatus of claim 61, further comprising a power cord connected to the housing and to the electrochemical cell for providing power to the electrochemical cell.

69. The apparatus of claim 61, further comprising a flush connected to the housing and the catholyte reservoir for flushing the catholyte reservoir.

70. The apparatus of claim 61, further comprising an external drain connected to the housing for draining the anolyte portion and the catholyte portion.

* * * * *

UNITED STATES PATENT AND TRADEMARK OFFICE
CERTIFICATE OF CORRECTION

| | |
|---|---|
| PATENT NO. | : 6,402,932 B1 |
| APPLICATION NO. | : 09/628720 |
| DATED | : October 30, 2007 |
| INVENTOR(S) | : Bruce W. Bremer and Roger W. Carson |

It is certified that error appears in the above-identified patent and that said Letters Patent is hereby corrected as shown below:

Title page,

Item (73) Assignee should read:

Scimist, Inc., Springfield, VA (US)

Signed and Sealed this
Fifteenth Day of May, 2012

David J. Kappos
*Director of the United States Patent and Trademark Office*

(12) EX PARTE REEXAMINATION CERTIFICATE (5981st)
United States Patent
Bremer et al.

(10) Number: US 6,402,932 C1
(45) Certificate Issued: Oct. 30, 2007

(54) MEDIATED ELECTROCHEMICAL OXIDATION OF BIOLOGICAL WASTE MATERIALS

(75) Inventors: Bruce W. Bremer, Montgomery Village, MD (US); Roger W. Carson, Vienna, VA (US)

(73) Assignee: The C & M Group, LLC, Vienna, VA (US)

Reexamination Request:
No. 90/007,610, Jun. 30, 2005

Reexamination Certificate for:
Patent No.: 6,402,932
Issued: Jun. 11, 2002
Appl. No.: 09/628,720
Filed: Jul. 28, 2000

Related U.S. Application Data
(60) Provisional application No. 60/145,972, filed on Jul. 29, 1999.

(51) Int. Cl.
*A62D 3/00* (2006.01)
*C02F 1/461* (2006.01)

(52) U.S. Cl. .................. 205/701; 588/304; 588/405; 588/310; 588/408; 588/320; 204/259; 204/263; 204/262; 204/252; 204/266; 205/688; 205/746; 205/703; 205/749

(58) Field of Classification Search ............. None
See application file for complete search history.

(56) References Cited

U.S. PATENT DOCUMENTS

| | | | | |
|---|---|---|---|---|
| 4,013,552 A | * | 3/1977 | Kreuter | 210/612 |
| 4,069,371 A | * | 1/1978 | Zito | 429/21 |
| 4,749,519 A | * | 6/1988 | Koehly et al. | |
| 4,810,995 A | * | 3/1989 | Kondou et al. | |
| 4,967,673 A | * | 11/1990 | Gunn | 110/346 |
| 5,047,224 A | * | 9/1991 | Dhooge | 423/437.1 |
| 5,261,336 A | * | 11/1993 | Williams | 110/264 |
| 5,380,445 A | * | 1/1995 | Rivard et al. | 210/748 |
| 5,516,972 A | * | 5/1996 | Farmer et al. | |
| 5,707,508 A | * | 1/1998 | Surma et al. | 205/688 |
| 5,756,874 A | * | 5/1998 | Steward | 588/302 |
| 5,911,868 A | * | 6/1999 | Balazs et al. | 205/688 |
| 5,919,350 A | * | 7/1999 | Balazs et al. | 205/688 |
| 5,952,542 A | * | 9/1999 | Steele | 588/303 |
| 5,968,337 A | * | 10/1999 | Surma et al. | 205/688 |
| 6,402,932 B1 | * | 6/2002 | Bremer et al. | 205/701 |

FOREIGN PATENT DOCUMENTS

| | | |
|---|---|---|
| DE | 4113817 A1 * | 11/1991 |
| DE | 4205739 A1 * | 8/1993 |
| WO | WO 97/15356 A1 * | 5/1997 |

OTHER PUBLICATIONS

The Second College Edition of the American Heritage Dictionary, 1985, p. 161.*
Chiba et al, "Mediated Electrochemical Oxidation as an alternative to Incineration for Mixed Wastes", which is a preprint from Laurence Livermore National Laboratory dated Feb. 1995.*
Davidson et al., "Ruthenium–Mediated Electrochemical Destruction of Organic Wastes", Platinum Metals Rev. (no month, 1998), vol. 42, No. 3, pp. 90–98.*
Morrison et al., "Structure and Properties", Organic Chemistry, Third Edition (no date), pp. 1–2.*

(Continued)

*Primary Examiner*—Alan Diamond

(57) ABSTRACT

A mediated electrochemical oxidation process is used to treat, oxidize and dispose of biological waste materials. Waste materials are introduced into an apparatus for contacting the waste with an electrolyte, which comprises one or more oxidizing species in their higher valence states in aqueous solution. The electrolyte, which can be regenerated, is used to oxidize specific molecules of the waste materials, breaking them down and preventing the formation of dioxins. The waste treatment process takes place at a temperature range from room temperature up to a temperature slightly below the boiling point of the electrolyte solution (usually the temperature will be below 100° C.), and can be altered by adding ultraviolet radiation.

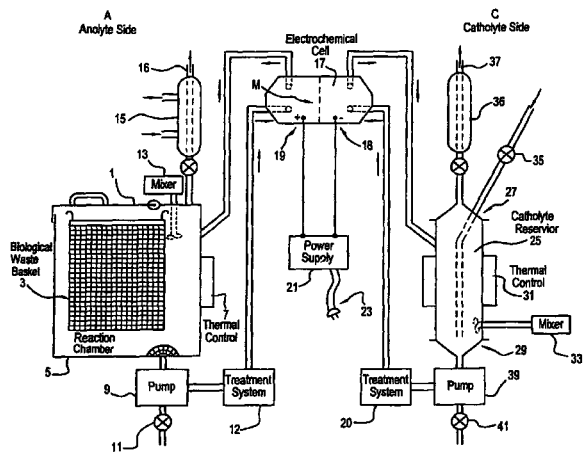

OTHER PUBLICATIONS

Pletcher et al., "Fundamental Concepts" and "Electrochemical Engineering", Industrial Electrochemistry, Second Edition (no month, 1990), pp. 1–172.*

Surma et al., "Catalyzed Electrochemical Oxidation (CEO) of Rocky Flats Contaminated Combustible Materials" (Mar. 1996), pp. 1–25.*

EOSystems, "Electrochem. Oxidation of Hazardous Organics" (Sep. 20, 1996), pp. 1–2.*

Whaley et al., "UNR Attacks Hazardous Waste Riddle", Las Vegas Review–Journal I Donrey Newspapers (Oct. 21, 1997), pp. 1–3.*

Hawley's Condensed Chemical Dictionary, Twelth Edition (no month, 1993), p. 1031.*

CIRIA, "Chemical Storage Tank Systems—Good Practice Guide", Summary Guidance Document, Publication No. W002, pp. 1–43.*

* cited by examiner

: US 6,402,932 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 11–13, 15, 21, 32, 33, 37, 39, 47, 54, 59, 69 and 70 are cancelled.

Claims 1, 2, 16, 23, 25–27, 36, 40–42, 44, 45, 48, 58 and 60 are determined to be patentable as amended.

Claims 3–10, 14, 17–20, 22, 24, 28–31, 34, 35, 38, 43, 46, 49–53, 55–57 and 61–68, dependent on an amended claim, are determined to be patentable.

New claims 71–100 are added and determined to be patentable.

1. A process for treating and oxidizing biological waste materials comprising disposing an electrolyte in an electrochemical cell, separating the electrolyte into an anolyte portion and a catholyte portion with a hydrogen ion-permeable membrane or porous polymer, ceramic or glass membrane, applying a direct current voltage between the anolyte portion and the catholyte portion, disposing a foraminous basket in the anolyte *portion in an anolyte reaction chamber*, placing or pouring the biological waste materials in the basket within the anolyte portion *in the anolyte reaction chamber*, and oxidizing the biological waste materials in the *basket within the* anolyte portion *in the anolyte reaction chamber* with a mediated electrochemical oxidation (MEO) process, wherein the anolyte portion further comprises an oxidizing species in aqueous solution *and wherein the oxidizing species reacts with the aqueous solution to produce powerful oxidizing free radicals,* and the electrolyte is an acid or neutral aqueous solution.

2. The process of claim 1, wherein [each of] the oxidizing species has *a* normal valence [states] *state* and *a* higher valence oxodizing [states] *state* and further comprising creating the higher valence oxidizing [states] *state* of the oxidizing species by stripping and reducing electrons off *the* normal valence state species in the electrochemical cell.

16. The process of claim 1, further comprising [involving] increasing the anolyte temperature above 50° C. thereby initiating reactions between the mediator and water to form the [free radical secondary oxidizing species] *powerful oxidizing free radicals* and hydrogen peroxide.

23. The process of claim 1, further comprising introducing more than one *type of* mediated oxidizing ion into the anolyte portion.

25. An apparatus for treating and oxidizing biological waste materials comprising an electrochemical cell, an electrolyte disposed in the electrochemical cell, a hydrogen ion-permeable membrane or porous polymers, ceramic, or a glass membrane disposed in the electrochemical cell for separating the cell into anolyte and catholyte *cell* chambers and separating the electrolyte into anolyte and catholyte portions, electrodes further comprising an anode and a cathode disposed in the electrochemical cell respectively in the anolyte and catholyte *cell* chambers and in the anolyte and catholyte portions of the electrolyte, a power supply connected to the anode and the cathode for applying a direct current voltage between the anolyte and the catholyte portions of the electrolyte, a foraminous basket disposed in [the] *an* anolyte *reaction* chamber *in the anolyte portion* for receiving the biological waste materials, an oxygen source connected to the electrochemical cell for promoting the oxidizing of the biological waste materials in the *anolyte reaction chamber in the* anolyte portion with a mediated electrochemical oxidation (MEO) process wherein the anolyte portion includes an oxidizing species in aqueous solution *and wherein the oxidizing species reacts with the aqueous solution to produce powerful oxidizing free radicals,* and the electrolyte is an acid, alkaline or neutral aqueous solution.

26. The apparatus of claim 25, wherein [each of] the oxidizing species has *a* normal valence [states] *state* and *a* higher valence oxidizing [states] *state* and wherein the higher valence oxidizing [states] *state* of the oxidizing species is created by stripping and reducing electrons off *the* normal valence state species in the electrochemical cell.

27. The apparatus of claim 25, further comprising an ultraviolet source connected to the anolyte *reaction* chamber and decomposing hydrogen peroxide into free hydroxyl radicals therein and increasing efficiency of the MEO process by recovering energy through the oxidizing of the biological waste materials in the anolyte *reaction* chamber.

36. The apparatus of claim 25, wherein the oxidizing [specie] *species* is chosen from the group consisting of silver, cerium, cobalt, iron, manganese, ruthenium, and combinations thereof.

40. The apparatus of claim [39] *25*, further comprising a thermal control connected to [a] *the* reaction chamber for varying the temperature of the anolyte portion.

41. The apparatus of claim [39] *25*, further comprising a condenser connected to the reaction chamber.

42. The apparatus of claim [39] *25*, further comprising a lid attached to the reaction chamber allowing insertion of waste into the anolyte portion.

44. The apparatus of claim [39] *25*, further comprising a filter connected to the reaction chamber.

45. The apparatus of claim [39] *25*, further comprising an anolyte pump connected to the reaction chamber for circulating the anolyte portion back to the electrochemical cell.

48. The apparatus of claim [39] *45*, further comprising an inorganic compounds removal and treatment system connected to the anolyte pump.

58. The apparatus of claim [51] *57*, further comprising a drain for draining catholyte connected to the catholyte pump.

60. The apparatus of claim [51] *57*, further comprising a metal recovery and acid treatment system connected to the catholyte pump.

*71. The process of claim 1, wherein the biological waste materials are selected from the group consisting of medical waste, infectious waste, pathological waste, animal waste and sanitary waste.*

*72. The apparatus of claim 25, wherein the biological waste materials are selected from the group consisting of medical waste, infectious waste, pathological waste, animal waste and sanitary waste.*

*73. The apparatus of claim 25, further comprising a lid on the anolyte reaction chamber above the foraminous basket, wherein the lid is raised to place the biological waste materials into the basket in the anolyte reaction chamber.*

*74. The process of claim 1, further comprising an anolyte reaction chamber housing anolyte and the basket with a lid on the reaction chamber above the foraminous basket, wherein the lid is raised to place the biological waste materials into the basket in the anolyte reaction chamber.*

*75. The process of claim 1, wherein the oxidizing species is iron, cobalt, manganese, ruthenium, silver or combinations thereof.*

*76. The apparatus of claim 25, wherein the oxidizing species is iron, cobalt, manganese, ruthenium, silver, or combinations thereof.*

*77. A process for treating and oxidizing biological waste materials, wherein the biological waste materials are selected from the group consisting of medical waste, infectious waste, pathological waste, animal waste and sanitary waste, comprising disposing an electrolyte in an electrochemical cell, separating the electrolyte into an anolyte portion and a catholyte portion with a hydrogen ion-permeable membrane or porous polymer, ceramic or glass membrane, applying a direct current voltage between the anolyte portion and the catholyte portion, operating the entire process at ambient atmospheric pressure, disposing a foraminous basket in the anolyte in an anolyte reaction chamber, further comprising the reaction chamber housing the basket with a lid on the anolyte reaction chamber above the foraminous basket, wherein the lid is raised to place the biological waste materials into the basket in the anolyte reaction chamber, placing or pouring the biological waste materials in the basket within the anolyte portion within the anolyte reaction chamber, and oxidizing the biological waste materials in the anolyte reaction chamber in the anolyte portion with a mediated electrochemical oxidation (MEO) process, wherein the anolyte portion further comprises an oxidizing species in aqueous solution that reacts with the aqueous solution to produce powerful oxidizing free radicals, and the electrolyte is an acid or neutral aqueous solution.*

*78. An apparatus for treating and oxidizing biological waste materials, wherein the biological waste materials are selected from the group consisting of medical waste, infectious waste, pathological waste, animal waste and sanitary waste, comprising an electrochemical cell, an electrolyte disposed in the electrochemical cell, a hydrogen ion-permeable membrane or porous polymers, ceramic or a glass membrane disposed in the electrochemical cell for separating the cell into anolyte and catholyte cell chambers and separating the electrolyte into anolyte and catholyte portions, electrodes further comprising an anode and a cathode disposed in the electrochemical cell respectively in the anolyte and catholyte cell chambers and in the anolyte and catholyte portions of the electrolyte, operating the entire apparatus at ambient atmospheric pressure, a power supply connected to the anode and the cathode for applying a direct current voltage between the anolyte and the catholyte portions of the electrolyte, a foraminous basket disposed in an anolyte reaction chamber in the anolyte portion for receiving the biological waste materials, an oxygen source connected to the electrochemical cell for promoting the oxidizing of the biological waste materials in the anolyte reaction chamber in the anolyte portion with a mediated electrochemical oxidation (MEO) process wherein the anolyte portion includes an oxidizing species in aqueous solution and wherein the oxidizing species reacts with the aqueous solution to produce powerful oxidizing free radicals, and the electrolyte is an acid, alkaline or neutral aqueous solution.*

*79. The apparatus of claim 78, wherein the oxidizing species is iron, cobalt, manganese, ruthenium, silver or combinations thereof.*

*80. The process of claim 77, wherein the oxidizing species is iron, cobalt, manganese, ruthenium, silver or combinations thereof.*

*81. The process of claim 77, further comprising circulating anolyte through the anolyte portion of the electrochemical cell.*

*82. The process of claim 77, further comprising contacting anolyte with biological waste materials in the anolyte reaction chamber.*

*83. The process of claim 77, further comprising introducing biological waste materials into the anolyte reaction chamber.*

*84. The process of claim 77, further comprising circulating catholyte through the catholyte portion of the electrochemical cell.*

*85. The process of claim 77, wherein the aqueous solution consists of water, mediator ions and the electrolytes chosen from the group consisting of acid and neutral electrolytes.*

*86. The apparatus of claim 78, further comprising a condenser connected to the anolyte reaction chamber.*

*87. The apparatus of claim 78, further comprising involving mediator ions with an oxidation potential sufficient to initiate secondary oxidation process as thereby producing additional oxidizers.*

*88. The apparatus of claim 78, wherein the aqueous solution consists of water, mediator ions and electrolytes chosen from the group consisting of acid, neutral, and alkaline electrolytes.*

89. The apparatus of claim 78, further comprising a catholyte reservoir off gas cleaning system for cleaning gases before release into the atmosphere connected to a catholyte reservoir.

90. The apparatus of claim 89, wherein the off gas cleaning system comprises scrubber/absorption columns.

91. The apparatus of claim 78, further comprising an air intake vent connected to a catholyte reservoir for introducing air to an air sparge.

92. The apparatus of claim 78, further comprising an external $CO_2$ vent connected to the anolyte reaction chamber for releasing $CO_2$ into the atmosphere.

93. The apparatus of claim 86, further comprising an external atmospheric vent connected to the condenser which is connected to the anolyte reaction chamber for releasing gases into the atmosphere.

94. The process of claim 77, wherein the treating and oxidizing biological waste materials further comprises a power supply that controls the DC voltage on the electrochemical cell.

95. The apparatus of claim 78, wherein the treating and oxidizing biological waste materials further comprises a power supply that varies the DC voltage on the electrochemical cell.

96. The process of claim 77, wherein the treating and oxidizing biological waste materials has by-products consisting of the following: carbon dioxide, water, oxygen, and inorganic compounds in the anolyte and hydrogen in the catholyte.

97. The apparatus of claim 78, wherein the treating and oxidizing biological waste materials has by-products consisting of the following: carbon dioxide, water, oxygen, and inorganic compounds in the anolyte and hydrogen in the catholyte.

98. The process of claim 77, wherein the waste materials are in the form of liquids, solids, or a mixture of liquids and solids.

99. The apparatus of claim 78, wherein the waste materials are in the form of liquids, solids, or a mixture of liquids and solids.

100. The apparatus of claim 78, wherein the treating and oxidizing biological waste materials further comprises a mediated electrochemical oxidation process operating in an automated mode under the control of an automated controller wherein the MEO process has safety features that provide for its safe operation in an indoor environment that has people present.

\* \* \* \* \*